United States Patent [19]

Pasqualini et al.

[11] 4,044,466

[45] Aug. 30, 1977

[54] DEVICE ESPECIALLY FOR ENDOOSSEOUS IMPLANTATION

[76] Inventors: Ugo Pasqualini, Via Borgonuovo, 26, Milan; Giovanni Russo, Via del Minatore, Verona, both of Italy

[21] Appl. No.: 578,566

[22] Filed: May 19, 1975

[30] Foreign Application Priority Data

May 30, 1974 Italy .................................. 23360/74

[51] Int. Cl.$^2$ ............................................. A61C 13/00
[52] U.S. Cl. ................................................. 32/10 A
[58] Field of Search ........................................ 32/10 A

[56] References Cited

U.S. PATENT DOCUMENTS

| 2,467,163 | 4/1949 | Skinner | 32/10 A |
| 2,857,670 | 10/1958 | Kiernan, Jr. | 32/10 A |
| 3,548,499 | 12/1970 | Valen | 32/10 A |
| 3,579,831 | 5/1971 | Stevens | 32/10 A |
| 3,623,226 | 11/1971 | Edelman | 32/10 A |
| 3,739,476 | 6/1973 | Roberts | 32/10 A |
| 3,837,080 | 9/1974 | Pasqualini | 32/10 A |
| 3,919,772 | 11/1975 | Lenczycki | 32/10 A |

*Primary Examiner*—Robert Peshock
*Attorney, Agent, or Firm*—Guido Modiano; Albert Josif

[57] ABSTRACT

A device especially for endoosseous implantation which comprises an appendix having at its free end a threaded portion which emerges into the oral cavity, an element joined to the appendix and housed in the cancellous tissue below the cortical of the jaw bones, and which comprises at least one through hole provided in the joint element and at least a stabilizing bar engaging with said hole which is supported at its ends by the vestibular and lingual cortical respectively.

1 Claim, 7 Drawing Figures

U.S. Patent
Aug. 30, 1977
4,044,466
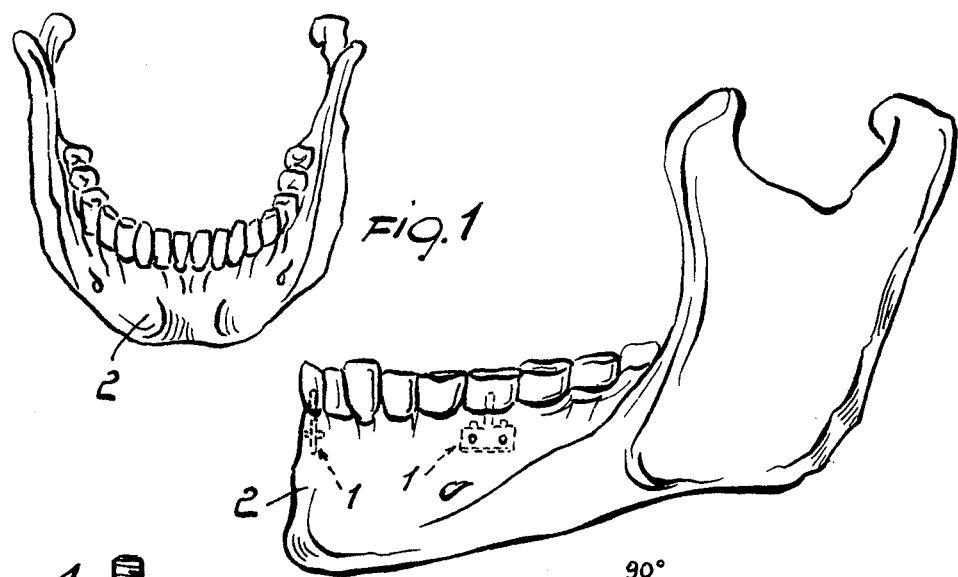
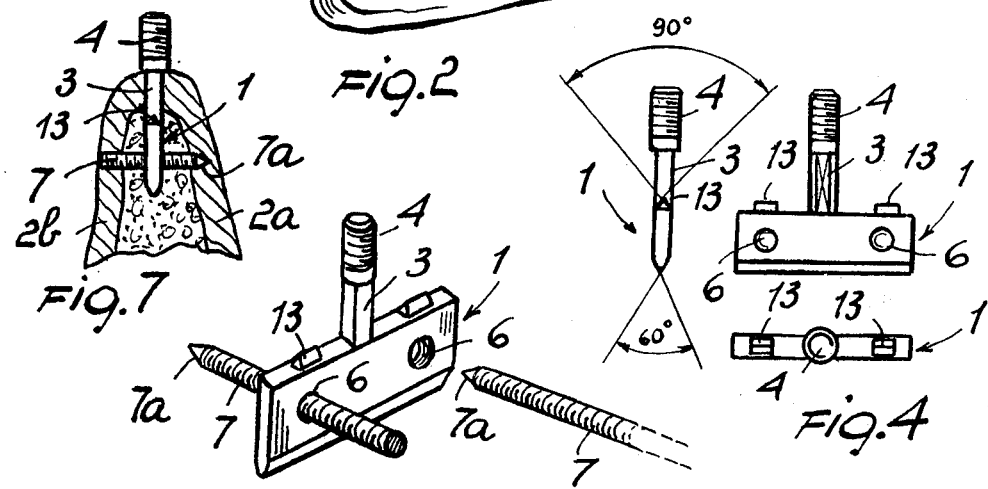
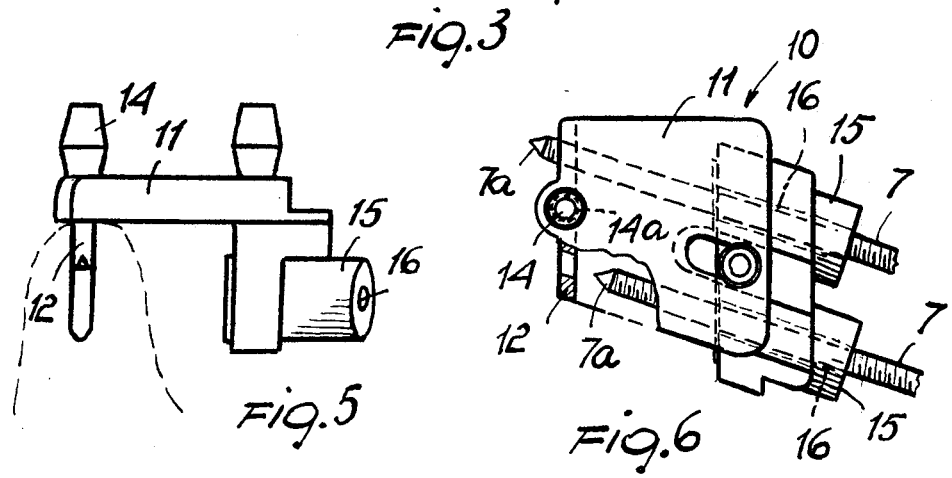

DEVICE ESPECIALLY FOR ENDOOSSEOUS IMPLANTATION

BACKGROUND OF THE INVENTION

This invention relates to a device especially for endoosseous implantation.

At the present time, in spite of the numerous positive results obtained with all types of endoosseous implantation (baskets, screws, foils, needles etc.) when carried out correctly in morphologically suitable zones and prosthetised without occlusal traumatism, the fact must be remembered that there is a preoccupying percentage of failures which unfortunately retard the generalisation of this recent therapy for edentulism.

The reasons for these failures are various and are not only due to lack of surgical skill, unsuitable zonal morphology or prosthetic trauma. One reason for failure, which has only recently been defined and overcome through the studies of one of the applicants, was related to the fact that in all devices, the endoosseous portion was immediately rigidly connected to the external portion projecting into the oral cavity (the stump). This subjected the device to the trauma deriving from the mechanical stresses transmitted by the stump during the delicate period of reparative osteogenesis of the surgical fissures necessary for the introduction of the devices.

To overcome the said disadvantage, it has been demonstrated in a previous patent that if the devices could remain without the external stump during the period of reparative osteogenesis, the failures were greatly reduced. In this type of device, the stump is screwed on only later when the osteogenesis has been completed by the deposition of mineral substances and the final transformation of the osteoblasts into osteocytes.

In spite of this, there still remained many obscure points to resolve, because all endoosseous devices are inserted below the cortical, but inevitably become housed in the cancellous bone, as notably represented by the interior of jaw bones.

There notably exists no possibility of transforming the cancellous bone into compact osseous tissue, even though sometimes osseous callus may induce into error.

From the foregoing, it can be seen that the endoosseous lamina may not become completely rigid, thus inevitably leading to failure of the operation.

The object of the present invention is to eliminate the aforementioned disadvantges by providing a device for endoosseous implantation which reliably guarantees stability, and completely prevents the occurrence of trauma of any type.

A further object of the present invention is to provide a device of simple and reliable application, and of high long-term reliability.

SUMMARY OF THE INVENTION

These and further objects, which will be more evident hereinafter, are attained by a device especially for endoosseous implantation, according to the invention, comprising an appendix with, at its free end, a threaded portion emerging into the oral cavity, and an element joined with said appendix housed in the cancellous bone below the cortical of the jaw bones, comprising at least one through hole provided in said joint element and at least one stabilising bar engaging with said at least one hole and supported at its ends by the vestibular cortical and the lingual cortical respectively.

BRIEF DESCRIPTION OF THE DRAWINGS

Further characteristics and advantages will be more evident from the description of one embodiment of a device for endoosseous implantation, illustrated by way of nonlimiting example in the accompanying drawing in which:

FIGS. 1 and 2 are a frontal and lateral view of a jaw bone;

FIG. 3 is a perspective view of the joint element with the stabilizing bars applied;

FIG. 4 is an elevational view, a lateral view and a view from above of the joint element;

FIG. 5 is a lateral view of the joint element with the relative positioning element;

FIG. 6 is a plan view of the positioning element and joint element;

FIG. 7 is a diagrammatic view of a joint element fixed in the cancellous bone below the cortical of the jaw bones.

DESCRIPTION OF A PREFERRED EMBODIMENT

With reference to said figures, the device for endoosseous implantation according to the invention comprises a joint element consisting of a plate element 1 for insertion into the cancellous bone below the cortical of the jaw bones, indicated overall by 2. The plate element 1 consists of a short narrow lamina, preferably but not necessarily made of titanium, which may also have other configurations according to the zonal morphology of the point at which it is applied.

An appendix 3 extends from the plate element 1 and comprises at its free end a threaded portion 4 which emerges into the oral cavity when the plate element is inserted below the cortical of the jaw bones 2.

Two threaded through holes 6 are provided in the blade element 1, each engaging with a threaded stabilising bar 7.

The stabilising bars 7 are supported at their ends by the lingual cortical indicated by 2a, and by the vestibular cortical indicated by 2b, respectively. More precisely, each stabilising bar 7 passes through the vestibular cortical 2b and its point 7a is supported in, or completely passes through the lingual cortical 2a.

As the stabilising bars 7 are screwed into the holes 6 when the plate element has been inserted into the cortical of the jaw bones 2, a positioning element, indicated by 10, is necessary to enable the bars 7 to be inserted into the holes 6, which under these conditions are not visible.

The positioning element 10 is provided for this purpose, and consists of a bridge element 11 comprising an arm 12 which is coupled by insertion with the plate element 1. More precisely, the insertion joint between the arm 12 and plate element 1 is formed by a pair of wedge elements 13 provided on that edge of the plate element 11 from which the appendix 3 extends, which couple with a pair of conjugate cavities provided at the free end of the arm 12.

At the arm 12, the positioning element 10 comprises a bush 14a which engages on the appendix 3, and a threaded plug 14 engages with the threaded portion 4 of the appendix 3, to make the positioning element 10 rigid with the plate element 1.

Guide cylinders 15, one for each hole 6, are supported on the bridge element 11 on the opposite side to the arm 12, and comprise innerly a smooth or possibly threaded cavity 16, the axis of which is aligned with the axis of the hole 6. The cylinders 15 are mounted on the bridge element 11 in such a manner that they can slide along the direction defined by the axis of the hole 16, so that the cylinders 15 can be positioned according to possible requirements.

A description will now be given of the application of the plate element 1 according to the invention inside the cancellous bone within the corticals of the jaw bones 2. The first part of the operation is similar to the classical method of LINKOW (incision of the fibromucosa, decollment, visualisation of the upper part of the osseous crest, creation of a surgical fissure and insertion of the plate element 1 into the cancellous bone). When the plate element 1 has been inserted into the cancellous bone, the positioning element 10 is connected to the plate element 1 by the threaded portion 4 and threaded plug 14, in the manner heretofore described. By this positioning, the guide cylinders 15 enable the transcortical channels to be prepared by means of the surgical fraise so that they pass through the vestibular cortical 2b and terminate in, or pass through the lingual cortical 2a, including the through hole 6 in their path. It is then extremely easy, by way of the guide cylinders 15, to perforate the vestibular cortical 2b, penetrate the adjacent cancellous bone, reach the threaded holes 6, pass through them, pass through the further cancellous bone and penetrate, to a certain extent or totally, the lingual cortical or palatine 2a. Once these two surgical channels have been made and the fraises extracted, the stabilising bars 7 are inserted in their place and, following the same path, they ultimately arrive at the lingual cortical 2a, having engaged with the said holes 6 provided in the plate element 1. As previously stated, the stabilising bars 7 are supported at their ends by the vestibular and lingual corticals and engage with the plate element 1 by way of the hole 6, and thus the plate element 1 is perfectly rigidly connected to the osseous tissue of the cortical of the jaw bones.

Once the stabilising bars 7 have been inserted, the positioning element 10 is removed and the projecting parts of the stabilising bars 7 are cut by a fraise to the level of the surface of the vestibular cortical 2b.

From the description it is evident that the device according to the invention attains all the proposed objects, and in particular it can be seen that it absolutely guarantees stability, so preventing the occurrence of any possible trauma.

The invention so conceived is susceptible to numerous modifications all of which fall within the scope of the inventive idea. Thus the holes 6, of which there are two in the described example, may be of any number, for example one or possibly more than two, according to the particular contingent requirements. The same applies to the configuration of the plate element 1, the dimensions of which will vary according to requirements.

Moreover all technical details may be replaced by others equivalent.

In practice the materials used, provided they are non-toxic, and the dimensions may be chosen at will according to requirements.

We claim:

1. A device for endoosseous implantation, comprising a plate member insertable into a surgical fissure provided into the cancellous tissue of the jaw bone, below the cortical tissue of the jaw bone, said plate member having on its oral cavity facing edge an appendix with, at its free end, a threaded portion emerging into the oral cavity, at least one through hole provided in said plate member and at least one stabilising bar engaging within said at least one hole and extending transverse to said plate member, said stabilizing bar being insertable into a respective surgical transcortical channel and having its ends supported by the vestibular cortical tissue and the lingual cortical tissue of the jaw bone respectively and positioning means removably connectable to said plate member for the preparation of said transcortical channel in alignment with said hole and for inserting said stabilising bar therein and in said hole, wherein said positioning means comprise a bridge element having an arm including connecting means for removable rigid connection with said plate member, said bridge element further comprising, on the side opposite said arm, at least one guide cylinder comprising an inner through cavity the axis of which is in alignment with the axis of said at least one hole when said positioning means is fixed on said plate member, said removable connecting means comprising a bush in said arm and engaging with said appendix and a threaded plug for removable engagement with the threaded portion of said appendix and wherein said removable connection means further comprise a pair of wedge projections on that edge of said plate element from which said appendix extends, and a pair of conjugate cavities provided in said arm.

* * * * *